(12) United States Patent
Barbosa

(10) Patent No.: US 11,195,633 B2
(45) Date of Patent: Dec. 7, 2021

(54) GALLIUM-68 GENERATORS AND METHODS FOR MAKING SUCH GENERATORS

(71) Applicant: Curium US LLC, St. Louis, MO (US)

(72) Inventor: Luis Antonio M. M. Barbosa, Bergen (NL)

(73) Assignee: Curium US LLC, St. Louis, MO (US)

( * ) Notice: Subject to any disclaimer, the term of this patent is extended or adjusted under 35 U.S.C. 154(b) by 428 days.

(21) Appl. No.: 16/325,862

(22) PCT Filed: Aug. 14, 2017

(86) PCT No.: PCT/US2017/046704
§ 371 (c)(1),
(2) Date: Feb. 15, 2019

(87) PCT Pub. No.: WO2018/035013
PCT Pub. Date: Feb. 22, 2018

(65) Prior Publication Data
US 2021/0280334 A1    Sep. 9, 2021

Related U.S. Application Data

(60) Provisional application No. 62/375,665, filed on Aug. 16, 2016.

(51) Int. Cl.
| | | |
|---|---|---|
| *C01B 39/06* | (2006.01) |
| *A61K 51/02* | (2006.01) |
| *G21G 1/00* | (2006.01) |
| *C01B 39/08* | (2006.01) |
| *C01G 15/00* | (2006.01) |
| *C01G 17/00* | (2006.01) |

(52) U.S. Cl.
CPC ........... *G21G 1/0005* (2013.01); *A61K 51/02* (2013.01); *C01B 39/065* (2013.01); *C01B 39/082* (2013.01); *C01G 15/00* (2013.01); *C01G 17/00* (2013.01); *C01P 2004/30* (2013.01)

(58) Field of Classification Search
CPC ..... C01B 39/065; C01B 39/082; A61K 51/02; C01G 15/00; C01G 17/00; G21G 1/08
See application file for complete search history.

(56) References Cited

U.S. PATENT DOCUMENTS

| | | |
|---|---|---|
| 4,264,468 A | 4/1981 | Neirinckx et al. |
| 4,333,911 A | 6/1982 | Comar et al. |
| 7,825,372 B2 | 11/2010 | Allberg |

OTHER PUBLICATIONS

Parsons, The Development of Zeolite Particles for Positron Imaging Applications, School of Chemistry College of Engineering and Physical Sciences University of Birmingham (Year: 2020).*

(Continued)

*Primary Examiner* — David M Brunsman
(74) *Attorney, Agent, or Firm* — Armstrong Teasdale LLP

(57) ABSTRACT

Gallium-68 generators that are capable of producing gallium-68 from a germanium-68 source material are disclosed. The source material may be a matrix material (e.g., zeolite) in which germanium-68 is isomorphously substituted for central atoms in tetrahedra within the matrix material. Methods for forming gallium-68 generators are also disclosed.

20 Claims, 2 Drawing Sheets

(56) References Cited

OTHER PUBLICATIONS

Rösh, Frank, "68Ge/68Ga Generators and 68Ga Radiopharmaceutical Chemistry on Their Way into a New Century", Journal of Postgraduate Medicine, Education and Research, Jan.-Mar. 2013; 47(1), 10.5005/jp-journals-10028-1052, pp. 18-25.

Keller, Cornelius, "Radiochemistry", John Wiley & Sons, English Edition, 1988, pp. 150-154.

Frick R et al., "Synthesis and Characterization of Ge-ZSM-5 Zeolites", J. Phys. Chem. Published 1993, pp. 5678-5684, vol. 97.

O'Keefe et al., "Germanate Zeolites: Contrasting the Behavior of Germanate and Silicate Structures Built from Cubic T8O20 Units (T=Ge or Si)", Chem. Eur. J., Published 1999, pp. 2796-2801, vol. 5.

Davis M et al., "Zeolite and Molecular Sieve Synthesis", Chem. Mater. Published 1992, pp. 756-768, vol. 4.

Davis M et al., "Zeolite from a Materials Chemistry Perspective", Chem. Mater. Published 2013, pp. A-G.

Moses et al., "Timing and Calibration in PET Using a Time Alignment Probe", IEEE Transactions on Nuclear Science. Published 2005, pp. 1-6, vol. LBNL-59117.

Zimmerman et al., "Calibrations of Large-Volume Solid Ge-68 Phantom Sources for Monitoring PET Scanner Performance in Clinical Trials", NIST Physical Measurement Laboratory. Published 2013, pp. 1.

"PET and PET-CT Ge-68 Reference and Calibration Sources", Epsilon Electronics. Published 2009, pp. 1-4.

Rimer et al., "Self-Assembly and Phase Behavior of Germanium Oxide Nanoparticles in Basic Aqueous Solutions", Langmui. Published 2007, pp. 2784-2791, vol. 23.

Davis et al., "Zeolites from a Materials Chemistry Perspective", Chemistry of Materials. Published 2013, pp. 239-245, vol. 26.

Cheng et al., "Preparation of 68Ge/68Ga generator with a binary Ga/Ag electrodepositions as solid target", Journal of Radioanalytical Chemistry. Published 2000, pp. 25-30, vol. 245.

Sen et al., "Choice of Inorganic Materials as 68Ge/68Ga Generator: An Intercomparison", Ion Exchange Letters. Published 2011, pp. 32-43, vol. 4.

"CT and PET/CT", GE HC. Published 2013, pp. 1-30.

F. Roesch: "Maturation of a Key Resource 1-21—The Germanium-68/Gallium-68 Generator: Development and New Insights", Current Radiopharmaceuticals, vol. 5, No. 3, Jun. 1, 2012 (Jun. 1, 2012), pp. 202-211, XP055422815, NL ISSN: 1874-4710, DOI: 10.2174/1874471011205030202 the whole document.

Kosslick H et al: "Synthesis and Characterization of Ge-ZSM-5 Zeolites", Journal of Physical Chemistry, American Chemical Society, US, vol. 97, No. 21, Jan. 1, 1993 (Jan. 1, 1993), pp. 5678-5684, XP002997494, ISSN: 0022-3654, DOI: 10.1021/J100123A036 the whole document.

PCT International Search Report and Written Opinion, Application No. PCT/US2017/046704, dated Nov. 21, 2017, 14 pps.

\* cited by examiner

GALLIUM-68 GENERATORS AND METHODS FOR MAKING SUCH GENERATORS

CROSS-REFERENCE TO RELATED APPLICATIONS

This application is a 35 U.S.C. § 371 national stage of International Application No. PCT/US2017/046704, filed Aug. 14, 2017, which claims the benefit of U.S. Provisional Patent Application No. 62/375,665 filed Aug. 16, 2016, both of which are incorporated herein by reference in their entirety.

FIELD OF THE DISCLOSURE

The field of the disclosure relates to gallium-68 generators that are capable of producing gallium-68 from a germanium-68 source material and to methods for producing gallium-68 generators that include such germanium-68 source material. The source material may be crystalline and germanium-68 may be isomorphously substituted for other central atoms of the crystalline matrix material.

BACKGROUND

Positron emission tomography (PET) is an in vivo imaging method that uses positron emitting radiotracers to track the biochemical, molecular, and/or pathophysiological processes in humans and animals. In PET systems, positron-emitting isotopes serve as beacons for identifying the exact location of diseases and pathological processes under study without surgical exploration of the human body. With these non-invasive imaging methods, the diagnosis of diseases may be more comfortable for patients, as opposed to the more traditional and invasive approaches, such as exploratory surgeries.

One such exemplary radiopharmaceutical agent group includes gallium-68 (Ga-68 or $^{68}$Ga), which may be obtained from the radioisotope germanium-68 (Ge-68 or $^{68}$Ge). Ge-68 has a half-life of about 271 days, decays by electron capture to Ga-68, and lacks any significant photon emissions. Ga-68 has a half-life of 68 minutes and decays by positron emission which makes gallium-68 an ideal isotope for medical radiotracing. Materials for holding the long-lived parent, Ge-68, are of significant interest as Ge-68 generates the shorter-lived gallium radioisotope.

Conventional materials for generating gallium-68 from germanium-68 include germanium-68 that is adsorbed onto the source material. The gallium-68 that is generated by decay of germanium-68 is eluted from the generator. The extraction liquid includes both gallium-68 and an amount of germanium-68 (which may be referred to as germanium-68 "breakthrough") that desorbs from the generator source material. After elution, the gallium-68 isotope is separated from germanium-68 and from other impurities, typically by column chromatography. Breakthrough of germanium-68 reduces the activity and yield of the generator.

There is a need for improved source materials that include Ge-68 to obtain Ga-68 for PET imaging such as materials that reduce germanium-68 breakthrough. There is also a need for related methods for producing such germanium-68 source materials.

This section is intended to introduce the reader to various aspects of art that may be related to various aspects of the disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

SUMMARY

One aspect of the present disclosure is directed to a generator for producing gallium-68 by decay of germanium-68. The generator includes a matrix material having a three-dimensional polyhedral crystal structure. The matrix material includes a first tetrahedra comprising a central atom, T, and oxygen, and has a formula $TO_4$. The central atom is selected from the group consisting of silicon, aluminum, zirconium and stable germanium. The matrix material includes a second tetrahedra. The second tetrahedra is a germanium-68 tetrahedra comprising germanium-68 and oxygen and has a formula $^{68}GeO_4$. The first tetrahedra and the germanium-68 tetrahedra are part of a three-dimensional polyhedral crystal structure. The generator includes a housing for holding the matrix material with the matrix material being within the housing. The generator includes a radiation shield to absorb radiation emitted by the matrix material.

Another aspect of the present disclosure is directed to a method for producing a gallium-68 generator that comprises a matrix material with germanium-68 isomorphously substituted therein. The method includes forming a crystallization starting mixture. The starting mixture has a source of a first central atom and a source of a second central atom. The first central atom is germanium-68 and the second central atom is selected from the group consisting of silicon, aluminum, zirconium and stable germanium. The starting mixture is heated to cause the material to crystallize and form germanium-68 tetrahedra and tetrahedra of the second central atom in a crystallized structure. The crystallized structure is encased in a generator housing.

Various refinements exist of the features noted in relation to the above-mentioned aspects of the present disclosure. Further features may also be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

DETAILED DESCRIPTION

Figure 1:
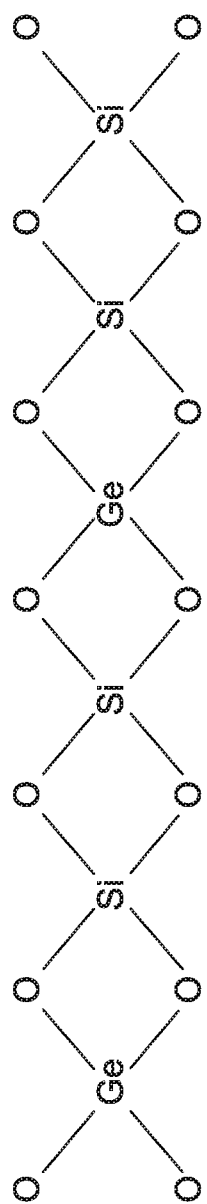
FIG. 1 is a schematic of a zeolite material in which germanium is isomorphously substituted for silicon central atoms.

Provisions of the present disclosure relate to generators for producing gallium-68 (which may be referred to as "germanium-68/gallium-68 generators") and to methods for producing such generators. The generator may include a crystallized matrix material having germanium-68 incorporated therein. The germanium-68 is isomorphously substituted for one or more central atoms in the crystallized matrix material.

The germanium-68 material of embodiments of the present disclosure may be any material (which may be referred to herein as "matrix material") which forms structures based on tetrahedral coordination. Generally the matrix material includes two different types of tetrahedra central atoms, one of which is germanium-68. Each tetrahedra atom has a central atom and a number (typically four) of coordination sites that are filled with oxygen. Each tetrahedral structure generally has a formula $TO_4$ wherein T is the central atom of the structure. The tetrahedra combine to form a polyhedral, three-dimensional crystal structure. Such three-dimensional structures may include various cavities or channels within the organized structure.

The central atoms, T, of the tetrahedra structures in the matrix material of embodiments of the present disclosure may be selected from silicon, aluminum, germanium and zirconium (e.g., $SiO_4$, $AlO_4$, $GeO_4$ and $ZrO_4$). In some embodiments, the matrix material comprises silicon tetrahedra ($SiO_4$) wherein germanium-68 is isomorphously substituted for silicon as the central atom of a number of tetrahedra within the matrix material. In this regard, it should be noted that the formula $TO_4$ as described herein represents the coordination of the tetrahedra (including shared oxygen) and that the material itself may have a different chemical formula. For example, the material itself may be silica ($SiO_2$), alumina ($AlO_2$), germania ($GeO_2$), zirconia ($ZrO_2$) and combinations of these materials with there being a tetrahedral coordination ($TO_4$) within the material.

The structure may be a zeolite material into which germanium-68 is isomorphously substituted for silicon. Zeolite material generally includes two or more different types of tetrahedra that are linked to form the polyhedral, three-dimensional crystal structure of the zeolite material. As used herein, "zeolite" refers to any matrix of a first type of central atom (typically silicon), a second type of central atom and oxygen. The various central atoms that may be used include silicon, aluminum, germanium and zirconium. For example, the zeolite may be a matrix of silicon and aluminum (silico-aluminates) or a matrix of silicon and germanium (silicogermanates) or even zirconium and germanium (zirconogermanates).

The zeolite material may be a natural zeolite that is modified to include germanium-68 as an isomorphous substitute for the various central atoms of the tetrahedral structures within the material. More typically, the zeolite is a synthetic zeolite with germanium-68 atoms being incorporated isomorphously while producing the material. In some embodiments, the zeolite contains both silicon and aluminum tetrahedra (i.e., is a silico-aluminate) with germanium-68 being substituted for some of the silicon and/or aluminum atoms in the tetrahedra structures. In some embodiments, the zeolite is a pentasil-zeolite (such as ZSM-5) which contains isomorphous germanium-68. In some embodiments, the zeolite material contains stable germanium tetrahedra and aluminum tetrahedra with germanium-68 being substituted for some of the germanium atoms and/or aluminum atoms.

In such zeolite structures, the zeolite typically comprises three tetrahedra structures—silicon tetrahedra, germanium-68 tetrahedra and a third tetrahedra selected from the group consisting of aluminum, zirconium and stable germanium. In some embodiments, the third central atom is aluminum tetrahedra, the aluminum tetrahedra comprising aluminum and oxygen and having a structure $AlO_4$. In other embodiments, the third tetrahedra is stable germanium tetrahedra, the stable germanium tetrahedra comprising stable germanium and oxygen and having a formula $GeO_4$.

The amount of germanium-68 in the matrix material may be consistent with amounts used in commercial germanium-68/gallium-68 generators. In some embodiments, formation of the crystallite material is controlled so as to form a matrix material with a particular activity range. In addition to germanium-68, the zeolite matrix material may contain non-active (i.e., stable) germanium (e.g., germanium-74) that is isomorphously incorporated for some of the central atoms of the tetrahedra structures (FIG. 1). The molar ratio of non-active germanium to germanium-68 in the zeolite may be controlled to form a generator with a desired activity. In some embodiments, the crystallized matrix material is combined with other materials such as various resins, binders, fillers or the like.

After formation, the germanium-68 substituted matrix material is placed within a column housing (e.g., glass column) that is surrounded by a radiation shield (e.g., lead shielded) to form the generator structure. The matrix material may be milled and/or sieved to control its particle size. After milling and/or sieving the matrix material may be packed into the column housing.

To generate gallium-68, a solvent (e.g., HCl, saline) may be introduced into the column to remove gallium-68 which has decayed from germanium-68. As gallium-68 has a different valence state as compared to germanium-68, (+3 for gallium-68 as compared to +4 for germanium-68), gallium-68 is less strongly bonded within the zeolite material. The energy released during decay exceeds the bond energy which allows the gallium-68 to be available for extraction from the column.

Hydrochloric acid (e.g., from about 0.05 M to about 2 M HCl) may be used as the eluent to extract gallium-68 from the column. The extraction solution may be further processed to remove impurities from the resulting eluant however, in some embodiments such further processing steps are eliminated. The extracted gallium-68 may be processed to form a radiopharmaceutical for medical use.

Matrix materials which incorporate germanium-68 may be obtained by including germanium-68 in starting mixtures from which the matrix is crystallized. By including germanium-68, germanium-68 isomorphously substitutes for various of the tetrahedral central atoms of the structure (e.g., silicon, aluminum, zirconium or stable germanium). The crystallization starting mixture may include a source of germanium-68 as first central atoms and a source of second central atoms. The second central atoms may be selected from the group consisting of silicon, aluminum, zirconium and stable germanium.

In some particular embodiments, germanium-68 is substituted for stable germanium that is used to assembly the structure. Zeolite materials incorporating stable germanium may be prepared according to known methods such as, for example, as described in Kosslick et al., "Synthesis and Characterization of Ge-ZSM-5 Zeolites", J. Phys. Chem. 1993, 97(21), pp. 5678-5684, which is incorporated herein by reference for all relevant and consistent purposes.

In some other embodiments, germanium-68 is substituted for an amount of silicon in the structure (e.g., up to about 30% of the silicon atoms). The molar ratio of germanium-68 to silicon in the starting mixture may be selected to achieve the desired activity and, as in some embodiments, may be at least about 1:1000, at least about 1:100, at least about 1:50, at least about 1:20, at least about 1:10 or at least about 1:5.

Matrix material such as zeolites may be prepared by forming an admixture or gel of the base material and maintaining crystallization conditions until crystals form. As crystals begin to form, the tetrahedra form a three dimensional network by sharing oxygen atoms.

In some embodiments, an aqueous mixture of germanium-68 oxide ($^{68}GeO_2$) and one or more other oxides is prepared (e.g., silica, alumina and/or stable germania) and heated to form crystals. As an alternative to use of germania, a germanium halide such as germanium chloride ($^{68}GeCl_4$) may be added to the zeolite formation mixture. Suitable crystallization conditions may include heating under hydrothermal conditions. For example, the crystallization starting mixture or gel may be heated to at least about 100° C. or even to at least about 150° C. (e.g., from about 100° C. to about 200° C.). Upon heating, the starting mixture crystallizes and forms tetrahedra of the first central atom and germanium-68 tetrahedra in the crystallized structure.

Suitable methods for forming the matrix material (e.g., zeolite material) may involve use of various structure directing agents (SDAs) including organic or inorganic agents which assist in formation of the three-dimensional structures. Exemplary SDAs include inorganic cations, phosphazenes, quaternary ammonium compounds (e.g., halides and hydroxides), imidazolium compounds and cyclic and linear ethers. Seed-assisted methods may also be used to promote crystallization and/or structure formation. Seed-assisted methods may involve use of seed crystals of the desired structure which act as crystal growth surfaces for formation of the matrix material.

After crystallization, the zeolite crystals may be separated from the liquid portion of the gel by filtration or evaporation. The crystals may be washed (e.g., with water) to remove residual liquids and fine crystals. In some embodiments, the crystalline material is calcined.

In some embodiments, the starting mixture is a gel having formula (1)

$$xGeO_2 ySiO_2 \qquad (1),$$

with (x, y) being (0.8, 0.2), (0.4, 0.6) or (0.165, 0.835).

In some embodiments, the second central atom is silicon. Alternatively or in addition, the starting mixture may comprise a source of third central atoms (such as in zeolite structures which also comprise germanium-68). If the second central atom is silicon, the third may be selected from the group consisting of aluminum, zirconium and stable germanium.

Figure 2:
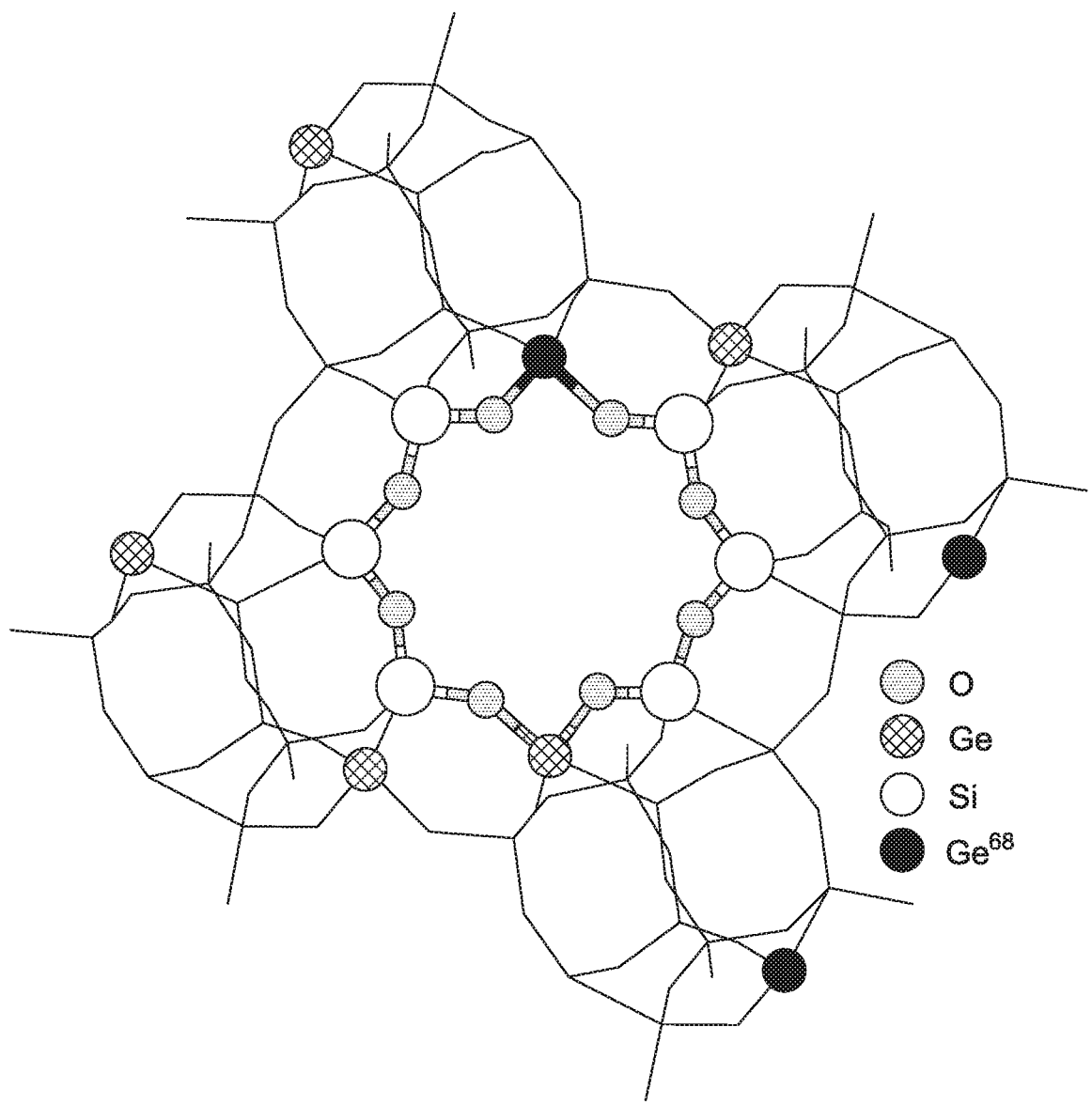
FIG. 2 is a schematic of a chabazite zeolite structure having a main cavity in an 8T ring with germanium-68 isomorphously being substituted for stable germanium.

The resulting germanium-68 zeolite frameworks may have any suitable shape such as, for example, cubic structures as described in O'Keeffe et al., "Germanate Zeolites: Contrasting the Behavior of Germanate and Silicate Structures being from Cubic $T_8O_{20}$ Units (T=Ge or Si)", Chem. Eur. J. 1999, 5 (10) which is incorporated herein by reference for all relevant and consistent purposes. Other frameworks such as Zeolite A (Linde Type A) or chains of 6-membered rings such as Zeolite Y (Linde Type Y) or chabazite, mordenite or ferrierite may also be prepared (see Davis et al., "Zeolite and Molecular Sieve Synthesis", Chem. Mater. 1992, 4(4) pp. 756-768 and Davis, "Zeolites from a Materials Chemistry Perspective," Chem. Mater., 2014, 26(1), pp. 239-245, both of which are incorporated herein by reference for all relevant and consistent purposes). An exemplary chabazite zeolite structure in which germanium-68 is isomorphously substituted a portion of non-active germanium atoms is shown in FIG. 2.

Compared to conventional germanium-68 containing materials, the matrix materials of embodiments of the present disclosure have several advantages. By isomorphously including germanium-68 into the framework and crystal structure of the material, germanium-68 does not need to be separately loaded onto the matrix material. This reduces the amount of loading material that may be lost due to loading and reduces waste (e.g., eliminates separate loading solutions). The material may be less contaminated with other stable metals (e.g., iron) and with radioactive metals (excluding other germanium isotopes) such as zinc-68 which is the decay product of gallium-68 as such impurity metals are less apt than germanium-68 to be incorporated into the matrix material. The support material is inorganic with high chemical, radiation and mechanical resistance relative to organic supports. Due to the different valence state of gallium, gallium is selectively released from the matrix material while germanium-68 may remain isomorphously bound to the material. By isomorphously incorporating germanium-68 into the matrix material, germanium-68 breakthrough is significantly reduced and post-processing steps for removal of germanium-68 may eliminated. By isomorphously binding geranium-68, the germanium-68 crystalline matrix material may be easily handled (e.g., less waste and easier packing) and eluted more easily.

As used herein, the terms "about," "substantially," "essentially" and "approximately" when used in conjunction with ranges of dimensions, concentrations, temperatures or other physical or chemical properties or characteristics is meant to cover variations that may exist in the upper and/or lower limits of the ranges of the properties or characteristics, including, for example, variations resulting from rounding, measurement methodology or other statistical variation.

When introducing elements of the present disclosure or the embodiment(s) thereof, the articles "a", "an", "the" and "said" are intended to mean that there are one or more of the elements. The terms "comprising," "including," "containing" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above constructions and methods without departing from the scope of the disclosure, it is intended that all matter contained in the above description and shown in the accompanying drawing[s] shall be interpreted as illustrative and not in a limiting sense.

What is claimed is:

1. A generator for producing gallium-68 by decay of germanium-68, the generator comprising:
   a matrix material having a three-dimensional polyhedral crystal structure, the matrix material comprising:
      a first tetrahedra comprising a central atom, T, and oxygen, the central atom being selected from the group consisting of silicon, aluminum, zirconium and stable germanium, the first tetrahedra having a formula $TO_4$;
      a second tetrahedra, the second tetrahedra being a germanium-68 tetrahedra comprising germanium-68 and oxygen and having a formula $^{68}GeO_4$, the first tetrahedra and germanium-68 tetrahedra being part of a three-dimensional polyhedral crystal structure,
   a housing for holding the matrix material, the matrix material being within the housing; and
   a radiation shield to absorb radiation emitted by the matrix material.

2. The generator for producing gallium-68 as set forth in claim 1 wherein the first tetrahedra is a silicon tetrahedra having a formula $SiO_4$, germanium-68 being isomorphously substituted for silicon as the central atom of a plurality of tetrahedra in the matrix material.

3. The generator for producing gallium-68 as set forth in claim 1 wherein the matrix material further comprises a third tetrahedra, the third tetrahedra comprising a central atom selected from the group consisting of silicon, aluminum, zirconium and stable germanium.

4. The generator for producing gallium-68 as set forth in claim 3 wherein the third tetrahedra is an aluminum tetrahedra, the aluminum tetrahedra comprising aluminum and oxygen and having a formula $AlO_4$.

5. The generator for producing gallium-68 as set forth in claim 3 wherein the third tetrahedra is a stable germanium tetrahedra, the stable germanium tetrahedra comprising stable germanium and oxygen and having a formula $GeO_4$.

6. The generator for producing gallium-68 as set forth in claim 5 wherein the stable germanium is isomorphously substituted for silicon as the central atom of a plurality of tetrahedra in the matrix material.

7. A method for producing gallium-68, the method comprising extracting gallium-68 from the gallium-68 generator as set forth in claim 1.

8. A method for producing a gallium-68 generator that comprises a matrix material with germanium-68 isomorphously substituted therein, the method comprising:
   forming a crystallization starting mixture, the starting mixture having a source of a first central atom and a source of a second central atom, the first central atom being germanium-68 and the second central atom being selected from the group consisting of silicon, aluminum, zirconium and stable germanium; and
   heating the starting mixture to cause the material to crystallize and form germanium-68 tetrahedra and tetrahedra of the second central atom in a crystallized structure; and
   encasing the crystallized structure in a generator housing.

9. The method a set forth in claim 8 wherein the second central atom is silicon.

10. The method as set forth in claim 9 wherein the crystallization starting mixture further comprises a third central atom selected from the group consisting of aluminum, zirconium and stable germanium, the crystallized structure comprising tetrahedra of the third central atom.

11. The method as set forth in claim 8 wherein the starting mixture is heated to at least about 100° C.

12. The method as set forth in claim 11 wherein the matrix material is crystallized under hydrothermal conditions.

13. The method as set forth in claim 8 wherein the first central atom is silicon, the molar ratio of germanium-68 to silicon in the starting mixture being at least about 1:1000.

14. The method as set forth in claim 8 wherein a germanium-68 halide is added to the starting mixture as a source of germanium-68.

15. The method as set forth in claim 8 wherein a $^{68}GeO_2$ is added to the starting mixture as a source of germanium-68.

16. The method as set forth in claim 8 wherein the second central atom is silicon, silica being added to the starting mixture as a source of silicon.

17. The method as set forth in claim 8 wherein the starting mixture is a gel, the gel comprising silica and stable germania according to the formula $$xGeO_2 ySiO_2.$$

18. The method as set forth in claim 17 wherein y is equal to (1-x) and x is 0.8, 0.4 or 0.165.

19. The method as set forth in claim 8 wherein the matrix material has a three-dimensional polyhedral crystal structure.

20. The method as set forth in claim 8 further comprising encasing the crystallized structure in a radiation shield.

* * * * *

UNITED STATES PATENT AND TRADEMARK OFFICE
CERTIFICATE OF CORRECTION

| | |
|---|---|
| PATENT NO. | : 11,195,633 B2 |
| APPLICATION NO. | : 16/325862 |
| DATED | : December 7, 2021 |
| INVENTOR(S) | : Barbosa |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 471 days.

Signed and Sealed this
Thirty-first Day of January, 2023

Katherine Kelly Vidal
*Director of the United States Patent and Trademark Office*